United States Patent [19]

Janssen et al.

[11] Patent Number: 5,128,479
[45] Date of Patent: Jul. 7, 1992

[54] OXIDIZED DIPHENYLHETEROALKANES

[75] Inventors: Bernd Janssen, Ludwigshafen; Hans-Heiner Wuest, Dossenheim, both of Fed. Rep. of Germany

[73] Assignee: BASF Aktiengesellschaft, Ludwigshafen, Fed. Rep. of Germany

[21] Appl. No.: 471,886

[22] Filed: Jan. 29, 1990

[30] Foreign Application Priority Data

Feb. 10, 1989 [DE] Fed. Rep. of Germany ....... 3903988

[51] Int. Cl.⁵ .................... C07C 69/76; C07D 257/04
[52] U.S. Cl. .................... 548/252; 548/253;
549/373; 549/374; 549/375; 549/451; 549/452;
549/453; 558/315; 558/415; 558/418; 558/423;
560/8; 560/10; 560/18; 560/45; 560/48;
560/51; 560/53; 560/56; 560/64; 560/66;
560/73; 560/107; 560/138; 560/139; 560/255;
562/46; 562/58; 562/74; 562/426; 562/432;
562/452; 562/457; 562/462; 562/463; 562/466;
562/473; 562/622; 564/162; 564/164; 564/165;
564/169; 564/171; 564/172; 564/173; 564/220;
564/221; 564/222; 564/342; 564/355; 564/363;
564/384; 564/440; 564/443; 568/31; 568/32;
568/41; 568/42; 568/55; 568/325; 568/327;
568/440; 568/441; 568/442; 568/630; 568/632;
568/734; 568/807; 568/808
[58] Field of Search ................ 424/428; 514/859, 863;
558/315, 415, 418, 423; 560/8, 10, 18, 45, 48,
51, 53, 56, 64, 66, 73, 107, 138, 139, 255;
562/426, 432, 452, 457, 462, 463, 466, 473, 622,
46, 58, 74; 564/162, 164, 165, 169, 171, 172,
173, 220, 221, 222, 342, 355, 363, 484, 440, 443;
548/252, 253; 549/373, 374, 375, 451, 453, 454;
568/31, 32, 41, 42, 55, 325, 327, 440, 441, 442,
630, 632, 734, 801, 805

[56] References Cited

U.S. PATENT DOCUMENTS 4,326,055  4/1982  Loeliger ..................... 568/426 X
4,582,857  4/1986  Grill et al. ..................... 514/563
4,588,750  5/1986  Boris ..................... 514/765

FOREIGN PATENT DOCUMENTS 0297995  1/1989  European Pat. Off. .
  3710  11/1966  France .
2164938  4/1986  United Kingdom .

OTHER PUBLICATIONS

Kuliev et al., Chemical Abstracts, vol. 96, (1980), 103768t.
Tanikaga et al., Chemical Abstracts, vol. 111, (1988), 77576k.
Lang et al., Chemical Abstracts, vol. 85, (1976), 46367h.
The Retinoids, vol. II, (1984), pp. 391-409, G. L. Peck, ed., M. B. Sporn et al.
The Medical Journal of Australia, vol. 146, (1987), pp. 374-377, R. Marks.
Drugs, vol. 34, (1987), pp. 459-503, C. E. Orfanos et al.

*Primary Examiner*—Richard L. Raymond
*Attorney, Agent, or Firm*—Oblon, Spivak, McClelland, Maier & Neustadt

[57] ABSTRACT

Oxidized diphenylheteroalkanes of the formula I

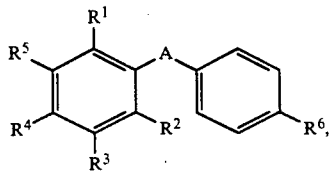

where $R^1$ to $R^6$ and A have the meanings specified in the description, and the preparation thereof are described. The substances are suitable for controlling diseases and as cosmetic agents.

4 Claims, No Drawings

OXIDIZED DIPHENYLHETEROALKANES

It has been disclosed that stilbene derivatives [cf. U.S. Pat. No. 4,326,055, GB 2,164,938 and U.S. Pat. No. 4,588,750] which contain the polyene structure of substances of the vitamin A type fixed in aromatic rings have pharmacological effects on topical and systemic therapy of neoplasms, acne, psoriasis and other dermatological disorders. The effect of these compounds is, however, not always satisfactory [cf. G. L. Peck in: The Retinoids, Vol. II (1984), 391–409, ed. M. B. Sporn et al., Academic Press N.Y., or R. Marks et al., Med. J. Australia 146 (1987) 374–377 or C. E. Orfanos et al., Drugs 34 (1987) 459–503].

The object of the present invention was to find compounds with an improved spectrum of action.

We have now found, surprisingly, that oxidized diphenylheteroalkanes of the formula I

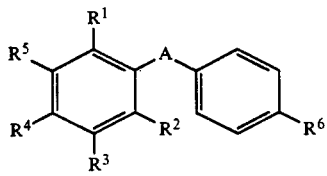

where A is one of the following: —CHOH—CH$_2$X— or —C(O)—CH$_2$X—, where X can be bonded to the left or right of the two phenyl rings and is oxygen, —S(O)$_n$— (with n being 0, 1 or 2) or NH; R$^1$, R$^2$ and R$^3$ are, independently of one another, hydrogen or C$_1$–C$_4$-alkyl; R$^4$ and R$^5$ are, independently of one another, hydrogen, C$_1$–C$_5$-alkyl or together, with the formation of a ring, —C(CH$_3$)$_2$—B—C(CH$_3$)$_2$— (with B being —CH$_2$CH$_2$— or —CH(CH$_3$)—) or —OC(CH$_3$)(Z)CH$_2$CH$_2$— (with Z being C$_1$–C$_2$-alkyl which can be substituted by —OR$^9$), and R$^4$ is additionally —OR$^9$; where R$^4$ and R$^5$ together form a ring of the said type when R$^1$ to R$^3$ are hydrogen; and R$^4$ and R$^5$ together form a ring of the said type or R$^3$ and R$^5$ are each branched C$_3$- or C$_4$-alkyl when R$^6$=H, OH, SH or CH$_3$; R$^6$ is hydrogen, methyl, cyano, tetrazolyl or —CH$_2$OR$^9$, —OR$^{10}$, —NR$^{11}$R$^{12}$, —CH$_2$NR$^{11}$R$^{12}$, —CH(OR$^{13}$)$_2$, —S(O)$_m$R$^{14}$ (with m=0, 1 or 2), —SR$^{10}$, —SO$_3$H or —COR$^{15}$, where R$^9$ is hydrogen, C$_{1-6}$-alkyl or C$_{1-6}$-alkanoyl, R$^{10}$ is hydrogen, C$_{1-6}$-alkyl, C$_{1-6}$-alkanoyl or benzoyl or —CH$_2$COR$^7$ (with R$^7$ being hydrogen, C$_{1-6}$-alkyl, C$_{1-6}$-alkoxy or hydroxyl), R$^{11}$ and R$^{12}$ are, independently of one another, hydrogen, C$_{1-4}$-alkyl, C$_{1-4}$-alkanoyl or benzyl or benzoyl, R$^{13}$ is C$_{1-6}$-alkoxy, it being possible for the two radicals to form together with the CH a cyclic 5- or 6-membered acetal, R$^{14}$ is C$_{1-6}$-alkyl, R$^{15}$ is hydrogen, hydroxyl, C$_{1-6}$-alkyl, C$_{1-6}$-alkoxy, phenoxy or benzyloxy, —NR$^{11}$R$^{12}$ with R$^{11}$ and R$^{12}$ being hydrogen, alkyl, or benzyl which can be substituted by hydroxyl or C$_{1-4}$-alkoxy, or —NR$^{16}$OR$^{17}$ (with R$^{16}$ and R$^{17}$=hydrogen or C$_1$–C$_3$-alkyl), and the physiologically tolerated salts thereof, where appropriate, have an improved spectrum of action.

Preferred compounds of the formula I are those where A is —XCH$_2$—C(O)— or —XCH$_2$—CHOH—, where X is linked to the phenyl on the left in the formula I and is oxygen, sulfur or —NH—.

Where R$^1$ and/or R$^2$ and/or R$^3$ are alkyl, branched alkyl is preferred over linear alkyl; if R$^4$ and R$^5$ together form —C(CH$_2$)$_2$—B—C(CH$_3$)$_2$—, B is preferably —CH$_2$CH$_2$—.

Further preferred compounds of the formula I are those in which R$^6$ is —CH$_2$OR$^9$, —OR$^{10}$, —SR$^{10}$, —SO$_2$R$^{14}$, —SO$_3$H or COR$^{15}$, and among these particularly preferred compounds are those in which R$^9$ is hydrogen, R$^{10}$ is hydrogen, acetyl, or benzoyl which is preferably substituted by amino, acetamino, dimethylamino, hydroxyl, methoxy or methylene groups or halogens, in particular fluorine or chlorine, R$^{14}$ is methyl or ethyl, R$^{15}$ is hydrogen, hydroxyamino, hydroxyl, methyl, ethoxy, or phenoxy which can be substituted by amino, acetamino, dimethylamino, hydroxyl or methoxy groups, or is —NR$^{11}$R$^{12}$ with R$^{11}$ and/or R$^{12}$ preferably being hydrogen, methyl, or benzyl which can be substituted by acetoxy, hydroxyl or methoxy groups.

Some of the novel compounds of the formula I contain chiral centers and are generally produced as diastereomer mixtures or racemates. The diastereomers can be separated, for example, by differences in solubility or by column chromatography, and isolated in pure form. Pure enantiomers can be obtained from the pairs of enantiomers by conventional methods. The present invention relates both to the pure enantiomers and to the mixtures thereof (racemates). Both the pure diastereomers or enantiomers and the mixtures thereof can be used as therapeutic or cosmetic agents.

Some of the compounds according to the invention have an acidic hydrogen and can therefore be converted with bases in a conventional manner into a physiologically tolerated salt which is readily soluble in water. Examples of suitable salts are ammonium and alkali metal salts, especially of sodium, potassium and lithium, and alkaline earth metal salts, especially of calcium or magnesium, as well as salts with suitable organic bases such as with lower alkylamines, e.g. methylamine, ethylamine or cyclohexylamine, or with substituted lower alkylamines, especially hydroxyl-substituted alkylamines, such as diethanolamine, triethanolamine or tris(hydroxymethyl)aminomethane and with piperidine or morpholine.

The amines of the formula I according to the invention can be converted by conventional methods into the acid addition salt of a physiologically tolerated acid. Examples of suitable physiologically tolerated organic or inorganic acids are: hydrochloric acid, hydrobromic acid, phosphoric acid and sulfuric acid, and of organic acids are maleic acid, fumaric acid, lactic acid, tartaric acid, malic acid, citric acid, salicylic acid, adipic acid and benzoic acid. Others can be found in "Fortschritte der Arzneimittelforschung" Volume 10, 1966, pages 224–225, Birkhäuser Verlag, Basle and Stuttgart.

The present invention also relates to a process for the preparation of the abovementioned compounds of the formula I by a) if A is —COCH$_2$X, reacting an acetophenone of the formula II

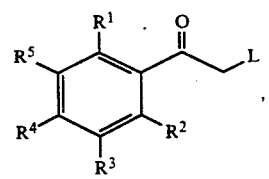

where $R^1$-$R^5$ have the abovementioned meanings, and L is a nucleofugic leaving group, e.g. halogen, preferably bromine or chlorine, or a reactive radical —$OR^{16}$ where $R^{16}$ is methylsulfonyl, trifluoromethylsulfonyl or toluenesulfonyl, with a benzene derivative of the formula III

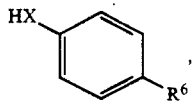

III where $R^6$ has the abovementioned meaning, and X is oxygen, sulfur or NH, in the presence of a base and, if X is sulfur, possibly oxidizing the resulting thioethers to the corresponding sulfoxides (X=SO) or sulfones (X=SO$_2$), b) if A is —XCH$_2$CO—, reacting an acetophenone of the formula IV

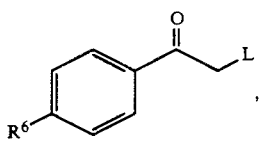

IV where $R^6$ has the abovementioned meaning, and L is a nucleofugic leaving group e.g. one of those mentioned in (a), with a benzene derivative of the formula V

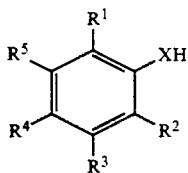

V where $R^1$-$R^5$ have the abovementioned meanings, and X is oxygen, sulfur or NH, in the presence of a base, and, if X is sulfur, possibly oxidizing the resulting thioethers to the corresponding sulfoxides (X=SO) or sulfones (X=SO$_2$), c) if A is —CH(OH)CH$_2$X—, either c1) reacting an oxirane of the formula VI

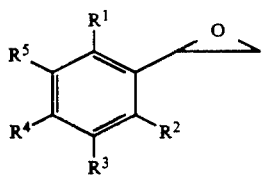

VI where $R^1$-$R^5$ have the abovementioned meanings, with a benzene derivative of the formula III and, if X is sulfur, possibly oxidizing the resulting thioethers to the corresponding sulfoxides (X=SO) or sulfones (X=SO$_2$), or c2) reducing the carbonyl group in a ketone of the formula VII obtained in process a)

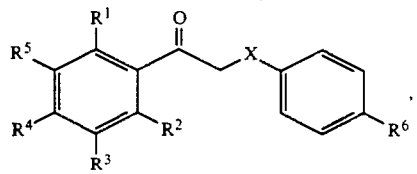

VII where $R^1$-$R^6$ and X have the abovementioned meanings, by a conventional method, d) if A is —XCH$_2$CH(OH)—, either d1) reacting an oxirane of the formula VIII

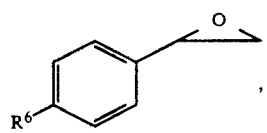

VIII where $R^6$ has the abovementioned meaning, with a benzene derivative of the formula V and, if X is sulfur, possibly oxidizing the resulting thioethers to the corresponding sulfoxides (X=SO) or sulfones (X=SO$_2$), or d2) reducing the carbonyl group in a ketone of the formula IX obtained in process b)

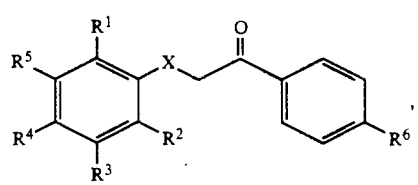

IX where $R^1$-$R^6$ and X have the abovementioned meanings, by a conventional method.

The alkylations a) and b) are carried out in a conventional manner, in the presence or absence of a solvent or diluent and with or without the addition of an inorganic or organic base and of a reaction accelerator at from 10° to 120° C., it being preferable to employ equimolar amounts of reactants II and III or IV and V, or one component can be in an excess of up to 10 mol-%. The preferred solvents or diluents include ketones such as acetone, methyl ethyl ketone or cyclohexanone, nitriles such as acetonitrile, esters such as ethyl acetate, ethers such as diethyl ether, tetrahydrofuran or dioxane, sulfoxides such as dimethyl sulfoxide, amides such as dimethylformamide, dimethylacetamide or N-methylpyrrolidone, as well as sulfolane, or mixtures thereof.

Examples of suitable bases, which can also be used as acid-binding agents in the reaction, are alkali metal carbonates such as sodium or potassium carbonate or sodium or potassium bicarbonate, pyridine or 4-dimethylaminopyridine. However, it is also possible to use other conventional bases.

Suitable and preferred reaction accelerators are metal halides such as sodium iodide or potassium iodide, quaternary ammonium salts such as tetrabutylammonium chloride, bromide or iodide, benzyltriethylammonium chloride or bromide, and crown ethers such as 12-crown-4, 15-crown-5, 18-crown-6, dibenzo-18-crown-6 or dicyclohexano-18-crown-6.

The reaction is generally carried out under atmospheric or superatmospheric pressure, continuously or batchwise.

When carrying out processes c1) and d1) according to the invention, 1 to 2 mole of the HX component III or V are preferably employed for 1 mole of oxirane VI or VIII, possibly with 1 to 2 mole of base. Suitable diluents are organic solvents which are inert under the reaction conditions. These preferably include alcohols such as ethanol, methoxyethanol or propanol; ketones such as acetone or 2-butanone; nitriles such as acetonitrile; esters such as ethyl acetate; ethers such as dioxane or tetrahydrofuran; aromatic hydrocarbons such as benzene or toluene; amides such as dimethylformamide or N-methylpyrrolidone; sulfoxides such as dimethyl sulfoxide, as well as sulfolane or mixtures thereof. Suitable bases for the reactions of processes c1) and d1) according to the invention are all conventionally usable inorganic and organic bases. These preferably include alkali metal carbonates such as sodium and potassium carbonates; alkalimetal hydroxides such as sodium hydroxide; alkali metal alcoholates such as sodium and potassium methylate and ethylate; alkali metal hydrides such as sodium hydride; and lower tertiary alkylamines, cycloalkylamines and aralkylamines such as, in particular, triethylamine.

The reaction temperatures can be varied within a relatively wide range. They are in general from 0° C. to 200° C., preferably from 60° C. to 150° C.

However, it is also possible to carry out processes c1) and d1) in the presence of basic alumina at room temperature.

Processes c2) and d2) are carried out by conventional methods for the reduction of ketone derivatives. This entails employing 1 to 3, preferably 1 to 1.5, equivalents of the reducing agent for 1 mole of the carbonyl compounds VII and IX.

Suitable reducing agents are metal hydrides such as diisobutylaluminum hydride, sodium, lithium and potassium hydride, borohydride or cyanoborohydride, as well as lithium aluminum hydrides of the general formula

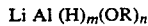
$$Li\ Al\ (H)_m(OR)_n$$

where m is 1 to 4 and n is 4−m, and where R can be identical or different and is generally alkyl, e.g. methyl, ethyl, propyl, isopropyl, n-butyl, isobutyl, tert-butyl or cyclohexyl, or hydrogen, in the presence or absence of a suitable catalyst, e.g. rhodium or ruthenium. Sodium borohydride is particularly preferred.

The reaction is generally carried out at from −20° to +120° C., preferably at −5° C. to +50° C., particularly preferably at 0° C. to +30° C., under atmospheric or super-atmospheric pressure, continuously or batchwise.

The thioethers (X=S) obtained by processes a)-d) according to the invention are, if desired, oxidized to the corresponding sulfoxides (X=SO) or sulfones (X=SO$_2$). The sulfoxides are prepared in the presence or absence of a solvent or diluent, and with or without the addition of a catalyst, by reacting 1.0 equivalent of the thioether with 1.0 to 1.1 equivalent of oxidizing agent at from −30° to 120° C.

The corresponding sulfones are prepared by using 2.0 to 3.0 equivalents of oxidizing agent. The preferred solvents or diluents include lower alkyl carboxylic acids such as formic acid, acetic acid and propionic acid, alcohols such as methanol, ethanol or isopropanol, hydrocarbons such as hexane, cyclohexane or heptane, aromatic compounds such as benzene, toluene or xylene, ethers such as methyl tert-butyl ether, diisopropyl ether or diphenyl ether, ketones such as acetone or methyl ethyl ketone, halohydrocarbons such as dichloromethane, chloroform, carbon tetrachloride, dichloroethane or chlorobenzene, as well as nitriles such as acetonitrile and propionitrile or amides such as dimethylformamide, dimethylacetamide or pyrrolidine, as well as water; however, mixtures thereof are also suitable.

Suitable oxidizing agents are the following: peroxy compounds such as hydrogen peroxide, tert-butylhydroperoxide, peracetic acid, perbenzoic acid, monoperphthalic acid and halogenated perbenzoic acids such as m-chloroperbenzoic acid. However, it is also possible to use other oxidizing agents such as potassium permanganate, potassium dichromate, sodium periodate or periodic acid as well as nitric acid and nitrous gases such as nitrogen dioxide (cf. for example "Methoden der Organischen Chemie" Ed. Eugen Müller, Vol. IX, pp. 207 et seq. and 223 et seq., Thieme Verlag, Stuttgart 1955, and Reid "Organic Compounds of Bivalent Sulfur", Vol. 2, pp. 64 et seq., Chem. Publ. Comp. New York, 1960).

Suitable catalysts are mineral acids such as hydrochloric acid or sulfuric acid, as well as alkali metal hydroxides such as sodium or potassium hydroxide and alkali metal carbonates such as sodium or potassium carbonate.

In cases where the reaction takes place in a two-phase system, it is possible to use phase-transfer catalysts, e.g. quaternary ammonium compounds such as tetrabutylammonium salts, to accelerate the reaction.

The starting compounds of the formula II (with L=hydrogen (e.g. DE-A 3,602,473, 3,434,942 and 3,434,944), chlorine or bromine) are either known or obtained by conventional methods for preparing acetophenones, for example by Friedel-Crafts acylation with acetic acid or chloro- or bromoacetic acid, the halides or anhydrides thereof (H. O. House: "Modern Synthetic Reactions", 2nd Ed., W.A. Benjamin Inc. Menlo Park, Calif.; 1972, pp. 797 et seq. and literature cited therein) or by oxidation of the corresponding ethylbenzenes (H. O. House, loc. cit., pp. 288 et seq. and literature cited therein). Compounds of the formula II (with L=hydrogen) obtained in this way are subsequently halogenated in a conventional manner (H. O. House, loc. cit., pp. 459-478 and literature cited therein).

The reactive esters of the formula II where L is —OR$^{16}$ are prepared from the corresponding ω-hydroxyacetophenones II (with L=OH) by conventional methods (Houben-Weyl-Müller, "Methoden der organischen Chemie", Georg Thieme Verlag, Stuttgart, 1955, Volume IX, pages 388, 663 and 671). Examples of such esters are methanesulfonates, trifluoromethanesulfonates, nonafluorobutanesulfonates, 4-methylbenzenesulfonates, 4-bromobenzenesulfonates, 4-nitrobenzenesulfonates and benzenesulfonates.

The starting compounds of the formula III are known or were obtained by conventional methods for the preparation of para-substituted anilines, phenols and thiophenols.

The starting compounds of the formula IV are known or can be prepared by conventional processes as described above for acetophenones of the formula II.

The starting compounds of the formula V are either known or can be obtained, in the case where X is oxygen, by the conventional methods for the preparation of substituted phenol derivatives ("Methoden der Organischen Chemie", Ed. Eugen Müller, Vol. VI/1c, pp.

4 et seq., 313 et seq., 925 et seq., Thieme Verlag, Stuttgart, 1976), or, in the case where X is sulfur, by the conventional processes for the preparation of thiophenols (K.-D. Gundermann and K. Hümke in "Methoden der Organischen Chemie", Vol. Ell, pp. 32 et seq., Thieme Verlag, Stuttgart, 1985 and literature cited therein). It is possible and preferable to prepare them by reduction of the corresponding sulfonic acid derivatives, for example with metal hydrides, or from the corresponding phenols of the formula II, which are converted into thiocarbamic esters (Newman and Karnes, J. Org. Chem. 31 (1966) 3980); or, in the case where X is NH, they are prepared in a conventional manner, for example by reduction of the corresponding nitro compounds ("Methoden der Organischen Chemie", Ed. E. Müller, Vol. XI/1, p. 394, Thieme Verlag, Stuttgart, 1957).

Most of the starting compounds of the formula VI are as yet unknown but they can be obtained in a conventional manner by reacting the appropriate benzaldehyde derivatives of the formula X

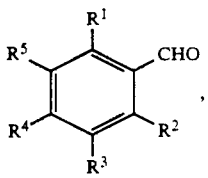

where $R^1$-$R^5$ have the abovementioned meanings, either α) with dimethyloxosulfonium methylide of the formula XI

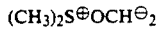

in a conventional manner in the presence of a diluent, for example dimethyl sulfoxide, at from 20° C. to 80° C. (cf. J. Am. Chem. Soc. 87 (1965) 1363–1364) or β) with trimethylsulfonium methyl sulfate of the formula XII

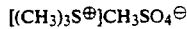

in a conventional manner in the presence of an inert organic solvent such as acetonitrile, and in the presence of a base such as sodium methylate, at from 0° C. to 60° C., preferably at room temperature (cf. heterocycles 8 (1977) 397).

The starting aldehydes of the formula X are either known or are obtained by conventional methods for the preparation of benzaldehydes, for example by Vilsmeier aromatic formylation (cf. De Meheas, Bull. Soc. Chem. Fr. (1962) 1989–1999 and literature cited therein) or by reduction of the corresponding benzoyl halides (cf. Fuson in: Patai, "The Chemistry of the Carbonyl Group", Vol. 1, pp. 211–232, Interscience Publ., N.Y. 1966 or Wheeler in: Patai, "The Chemistry of Acyl Halides", pp. 231–251, Interscience Publ. N.Y. 1972) or of the corresponding benzonitriles (cf. J. March: "Advanced Organic Chemistry, 2nd Ed., McGraw-Hill Kogakusha Ltd, Tokyo, 1977, pp. 835–836 and literature cited therein).

Some of the starting compounds of the formula VIII are known; they are preferably prepared from the corresponding benzaldehydes of the formula XIII

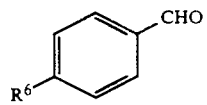

where $R^6$ has the abovementioned meaning, in a process similar to that indicated above for the preparation of oxiranes of type VI. Most of the starting aldehydes of the formula XIII are known, or they are obtained in a conventional manner as indicated above for aldehydes of the formula X.

The substances prepared by the abovementioned processes a–d can subsequently be further modified as follows:

The benzoic esters of the formula I ($R^6$=carboalkoxy) are, if desired, hydrolyzed to give the free carboxylic acids. Of course, it is conversely possible to esterify the free acid in a conventional manner.

The hydrolysis/esterification is expediently carried out in the presence of a diluent or solvent, for example a dialkyl glycol ether or cyclic ether, such as 1,2-dimethoxyethane, tetrahydrofuran or dioxane, or a lower aliphatic ketone such as acetone, methyl ethyl ketone or methyl isobutyl ketone, or in a lower aliphatic alcohol such as methanol, ethanol, propanol or isopropanol, or in dimethyl sulfoxide, or in mixtures of the said solvents with water.

Preferred solvents are aqueous mixtures of ethanol, methanol and dimethyl sulfoxide, in which case the reaction is carried out at the boiling point of the reaction mixture.

The hydrolysis is preferably carried out in the presence of alkali, such as alkali metal hydroxides, carbonates or bicarbonates, especially of sodium or potassium, organic tertiary bases such as pyridine or lower trialkylamines, such as trimethyl- or triethylamine, mixed with water. The ratio of the base to the ester is stoichiometric, or the base is employed in slight excess. Sodium or potassium hydroxide is preferably used.

The esterification is advantageously carried out by first converting the carboxylic acid into its salt and treating the latter with an appropriate alkyl halide, preferably an alkyl bromide or iodide. Particularly suitable deprotonating agents for preparing the salts in situ are the carbonates, hydroxides and hydrides of the alkali metals.

It is expedient to use aprotic polar solvents such as acetone, dimethylformamide, dimethyl sulfoxide and, in particular, methyl ethyl ketone, in which case the reaction is carried out at the boiling point of the reaction mixture.

The amides of the general formula I according to the invention can be prepared in a conventional manner by converting the benzoic acid I ($R^6$=COOH) into activated derivatives, e.g. into the carbonyl halides, azides, imidazolides or anhydrides, the O-acyl-N,N'-dicyclohexylisoureas or p-nitrophenylesters, and treating the latter with amines $HNR^{11}R^{12}$. In the case of particularly reactive amines, especially ammonia, the direct aminolysis of esters (with $R^6$=$COR^{15}$ and $R^{15}$ being alkoxy) is preferred.

The hydroxamic acid derivatives of the general formula I according to the invention are prepared by converting benzoic acids of the formula I ($R^6$=$CO_2H$) into activated derivatives, as indicated above, and subsequently reacting the latter with hydroxylamine or derivatives thereof, HNR$^{16}$OR$^{16}$, in an inert organic solvent, with or without the addition of an organic or inorganic base as proton trap, preferably at room temperature or else at elevated temperature, under atmospheric or superatmospheric pressure.

When hydroxylamine is the reactant, it is preferably employed as a salt, e.g. as hydrochloride, and the reaction is carried out using 2 equivalents of base, e.g. triethylamine or potassium carbonate, in dimethylformamide.

A carboxylic acid or ester or amide thereof of the formula I (R$^6$=C(O)R$^{15}$) can be reduced in a conventional manner to the corresponding alcohols or amines. The reduction is advantageously carried out with a metal hydride or alkali metal hydride in the presence of a suitable solvent. Preferred metal hydrides are complex metal hydrides such as lithium aluminum hydride or diisobutylaluminum hydride. The solvents used with lithium aluminum hydride are ethers such as diethyl ether, dioxane or tetrahydrofuran. If the reduction is carried out with diisobutylaluminum hydride or a sodium alkoxyaluminum hydride, it is preferable to use hydrocarbons such as hexane or toluene.

Amines or alcohols obtained in this way can be converted in a conventional manner using an alkanoyl halide or anhydride or an aroyl halide or anhydride, expediently in an inert diluent or solvent, e.g. in a lower aliphatic ketone such as acetone, methyl ethyl ketone or methyl isobutyl ketone or a dialkylformamide such as dimethylformamide or diethylformamide, or with excess acylating agent as diluent or solvent, into the amides and esters of the formula I according to the invention. The reactions are preferably carried out in the presence of a base as acid-binding agent at from −20° C. to the boiling point of the reaction mixture. Suitable bases are alkali metal carbonates, bicarbonates, hydroxides or alcoholates, especially of sodium and potassium, basic oxides such as aluminum oxide or calcium oxide, organic tertiary bases such as pyridine or lower trialkylamines such as trimethyl- or triethylamine. In relation to the acylating agent employed, the bases can be used in a catalytic amount or the stoichiometric amount or in a slight excess.

An alcohol of the formula I (R$^6$=CH$_2$O R$^9$, R$^9$=H) can be etherified with alkyl halides R$^9$—I, R$^9$—Br or R$^9$—Cl in the presence of alkali metal hydrides, preferably sodium hydride, or in the presence of alkyllithium compounds, preferably n-butyllithium, in an organic solvent such as tetrahydrofuran, dioxane, 1,2-dimethoxyethane methyl tert-butyl ether or, when sodium hydride is used, also in dimethylformamide, at from −10° C. to 40° C.

An alcohol of the formula I can be oxidized to the corresponding aldehyde with suitable oxidizing agents, preferably manganese(IV) oxide, which can be on an inorganic support such as silica gel or alumina. This is advantageously carried out in an inert organic solvent, for example a hydrocarbon such as hexane, or in an ether such as tetrahydrofuran, or in mixtures of the said solvents and diluents, at from −10° C. to 30° C. The reaction time essentially depends on the oxidizing activity of the manganese(IV) oxide employed.

An aldehyde I (R$^6$=—CHO) can be obtained by reducing the corresponding nitrile with diisobutylaluminum hydride in a solvent, preferably in toluene, hexane, tetrahydrofuran or mixtures of these solvents, at from −40° C. to room temperature.

Aldehydes and ketones of the formula I are also obtained by hydrolyzing their acetals, conventionally in the presence of an acid as catalyst, preferably dilute hydrochloric or sulfuric acid, at from 20° C. up to the boiling point of the reaction mixture. The reaction is expediently carried out in water-miscible solvents such as acetone, dioxane or tetrahydrofuran, preferably in short-chain alcohols such as methanol and ethanol.

A nitrile of the formula I (R$^6$=—CN) can be hydrolyzed in a conventional manner with acid or, more advantageously, base catalysis to the corresponding carboxylic acid. Preferred bases are alkali metal hydroxides, especially potassium hydroxide, which is employed in excess. The solvents normally used are water-miscible alcohols such as methanol, ethanol, isopropanol and n-butanol. The reaction is usually carried out at the boiling point of the reaction mixture.

The nitriles I (R$^6$=—CN) can be converted by addition of an azide, e.g. an alkali metal azide, preferably sodium azide, in the presence of aluminum chloride or ammonium chloride, into the corresponding tetrazoles. The preferred solvents are cyclic ethers such as dioxane or tetrahydrofuran as well as, in particular, dimethylformamide or mixtures thereof, the reaction generally taking place at from 60° to 100° C.

The acylated phenols of the general formula I (R$^6$=—OR$^{10}$ with R$^{10}$=C$_1$-C$_6$-alkanoyl) are converted, if desired, into the free phenols and their physiologically tolerated salts by hydrolysis. The hydrolysis is expediently carried out in the presence of a diluent, for example a water-miscible ether, such as 1,2-dimethoxyethane or tetrahydrofuran, or a lower aliphatic alcohol such as methanol, ethanol, propanol, isopropanol or butanol, or in mixtures of the said solvents with water Preferred solvents are aqueous mixtures of ethanol or methanol, in which case the reaction is carried out at from 20° C. to the boiling point of the reaction mixture. The hydrolysis is preferably carried out in the presence of hydroxides or carbonates of the alkali metals or alkaline earth metals, especially sodium and potassium.

A phenol of the formula I can be converted into the esters according to the invention in a conventional manner using an alkanoyl halide or anhydride or an aroyl halide or anhydride, expediently in an inert diluent or solvent, e.g. a lower aliphatic ketone such as acetone, methyl ethyl ketone or methyl isobutyl ketone or a dialkylformamide such as dimethylformamide or diethylformamide, or with excess acylating agent as diluent or solvent. The reactions are preferably carried out in the presence of a base as acid-binding agent at from −20° C. to the boiling point of the reaction mixture. Suitable bases are alkali metal carbonates, bicarbonates, hydroxides or alcoholates, especially of sodium and potassium, basic oxides such as aluminum oxide or calcium oxide, organic tertiary bases such as pyridine or lower trialkylamines such as trimethyl- or triethylamine. In relation to the alkylating agent employed, the bases can be used in a catalytic amount or the stoichiometric amount or in a slight excess.

The etherification of the phenols of the formula I to aryl ethers of the formula I is advantageously carried out by first converting the phenol into its salt, and treating the latter with an appropriate alkyl halide or sulfate, preferably an alkyl chloride, bromide or iodide. Particularly suitable deprotonating agents for the preparation of the phenolates in situ are the carbonates, hydroxides and hydrides of the alkali metals. It is expedient to use aprotic polar solvents such as acetone, dimethylformamide, dimethyl sulfoxide or methyl ethyl ketone, in which case the reaction is carried out at from 20° C. to the boiling point of the reaction mixture.

The acylated thiophenols of the general formula I ($R^6=-SC(O)R^{14}$ with $R^{14}=C_1-C_6$-acyl) are converted, if desired, into the free thiophenols and their physiologically tolerated salts by hydrolysis. The hydrolysis is expediently carried out in the presence of a diluent, for example a water-miscible ether, such as 1,2-dimethoxyethane or tetrahydrofuran, or a lower aliphatic alcohol such as methanol, ethanol, propanol, isopropanol or butanol, or in mixtures of the said solvents with water. Preferred solvents are aqueous mixtures of ethanol or methanol, in which case the reaction is carried out at from 20° C. to the boiling point of the reaction mixture. The hydrolysis is preferably carried out in the presence of hydroxides or carbonates of the alkali metals or alkaline earth metals, especially of sodium and potassium.

A thiophenol of the formula I can be converted into the thioesters according to the invention in a conventional manner using an alkanoyl halide or anhydride or an aroyl halide or anhydride, expediently in an inert diluent or solvent, e.g. a lower aliphatic ketone such as acetone, methyl ethyl ketone or methyl isobutyl ketone or a dialkylformamide such as dimethylformamide or diethylformamide, or with excess acylating agent as diluent or solvent. The reactions are preferably carried out in the presence of a base as acid-binding agent at from −20° C. to the boiling point of the reaction mixture. Suitable bases are alkali metal carbonates, bicarbonates, hydroxides or alcoholates, especially of sodium and potassium, basic oxides such as aluminum oxide or calcium oxide, organic tertiary bases such as pyridine or lower trialkylamines such as trimethyl- or triethylamine. In relation to the alkylating agent employed, the bases can be used in a catalytic amount or the stoichiometric amount or in a slight excess.

The etherification of the thiophenols of the formula I to aryl thioethers of the formula I is advantageously carried out by first converting the thiophenol into its salt, and treating the latter with an appropriate alkyl halide or sulfate, preferably an alkyl chloride, bromide or iodide. Particularly suitable deprotonating agents for the preparation of the thiophenolates in situ are the carbonates, hydroxides and hydrides of the alkali metals. It is expedient to use aprotic polar solvents such as acetone, dimethylformamide, dimethyl sulfoxide or methyl ethyl ketone, in which case the reaction is carried out at from 20° C. to the boiling point of the reaction mixture.

The thioethers of the formula I ($R^6=-S-C_1-C_6$-alkyl) according to the invention are, if desired, converted into the corresponding sulfoxides or sulfones. The oxidation to sulfoxides is advantageously carried out by reacting the thioethers in alcoholic solution with equimolar amounts or not more than a 10% excess of periodic acid or of an alkali metal salt thereof, preferably with the sodium salt, at from 0° to 30° C. Examples of suitable solubilizers are water, dimethyl sulfoxide or amides such as dimethylformamide, as well as ketones such as acetone. The oxidation to sulfones is advantageously carried out by allowing 2.0 to 3.0 equivalents of the oxidizing agent to act on the appropriate thioether at from −30° to 120° C., preferably −10° to 60° C. Other suitable oxidizing agents are hydrogen peroxide and, in particular, peroxycarboxylic acids, of which m-chloroperoxybenzoic acid is preferred. Preferred solvents when hydrogen peroxide is used are acetic acid and acetonitrile, and when peroxycarboxylic acids are used are aprotic solvents such as methylene chloride or toluene.

The thiophenols of the formula I ($R^6=SH$) can, if desired, be converted into the corresponding sulfonic acids by allowing from 2 to 5 times the molar amount of hydrogen peroxide to act on the thiophenol, preferably in acetic acid, at from 10° C. to the boiling point of the reaction solution.

Acid or alkaline hydrolysis of the N-acylated amines of the formula I ($R^6=-NH-C_{1-4}$-alkanoyl or -benzoyl) according to the invention yields the corresponding aniline derivatives ($R^6=NH_2$). The hydrolysis is expediently carried out in the presence of a solvent or diluent, for example a dialkyl glycol ether or cyclic ether, such as 1,2-dimethoxyethane, tetrahydrofuran or dioxane, a lower aliphatic ketone such as acetone, methyl ethyl ketone or methyl isobutyl ketone, or in a lower aliphatic alcohol such as methanol, ethanol, propanol or isopropanol or in mixtures of the said solvents with water.

Preferred solvents are aqueous mixtures of ethanol and methanol, in which case the reaction is carried out at the boiling point of the reaction mixture.

The alkaline hydrolysis is carried out in the presence of alkali, such as alkali metal hydroxides, carbonates or bicarbonates, especially of sodium or potassium, organic tertiary bases such as pyridine or lower trialkylamines, such as trimethyl- or triethylamine, mixed with water. The ratio of the base to the ester is stoichiometric, or the base is employed in slight excess. Sodium or potassium hydroxide is preferably used.

The acid hydrolysis is carried out in the presence of mineral acids such as hydrochloric acid, sulfuric acid or phosphoric acid, or of organic acids such as benzenesulfonic acid or toluenesulfonic acid. The ratio of acid to ester is stoichiometric, or the acid is employed in slight excess. Hydrochloric acid is preferably used.

Anilines ($R^6=NH_2$) obtained in this way can be converted in a conventional manner using an alkanoyl halide or anhydride or an aroyl halide or anhydride or an alkyl or benzyl halide, expediently in an inert diluent or solvent, e.g. a lower aliphatic ketone such as acetone, methyl ethyl ketone or methyl isobutyl ketone or a dialkylformamide such as dimethylformamide or diethylformamide, or with excess acylating agent as diluent or solvent, into the amines and amides of the formula I ($R^6=NR^{11}R^2$) according to the invention. The reactions are preferably carried out in the presence of a base as acid-binding agent at from −20° C. to the boiling point of the reaction mixture. Examples of suitable bases are alkali metal carbonates, bicarbonates, hydroxides or alcoholates, especially of sodium and potassium, basic oxides such as aluminum oxide or calcium oxide, organic tertiary bases such as pyridine or lower trialkylamines such as trimethyl- or triethylamine. In relation to the acylating or alkylating agent, the bases can be used in a catalytic amount or the stoichiometric amount or in a slight excess.

The compounds according to the invention and their physiologically tolerated salts can, by reason of their pharmacological properties, be used for the topical and systemic therapy and prophylaxis of precanceroses and carcinomas of the skin, the mucous membranes and internal organs and for the topical and systemic therapy of acne, psoriasis and other dermatological disorders associated with pathological keratinization, especially ichthyosis, Darier's disease, herpes and leukoplakia, but also vitiligo, eczema, warts, phototoxis (premature aging) of the skin, and dry eyes and other corneopathies and for the treatment of rheumatic disorders, especially those of an inflammatory or degenerative nature and which affect joints, muscles, tendons and other parts of the locomotor system. Preferred indications are: the therapy of dermatological disorders, of skin damage caused by sunlight, and of iatrogenic skin damage, e.g. atrophy induced by corticosteroids, and the prophylactic treatment of precanceroses and tumors.

The pharmacological effects can be shown, for example, in the following tests: the compounds according to the invention abolish the keratinization which starts in hamster tracheal tissue in vitro after vitamin A deficiency. The keratinization is part of the early phase of carcinogenesis, which is inhibited by the compounds of the formula I according to the invention in a similar test in vivo after initiation by chemical compounds, by energetic radiation or after viral cell transformation. These methods are described in Cancer Res. 36 (1972) 964–972 and Nature 250 (1974) 64–66 and 253, (1975) 47–50.

In addition, the compounds according to the invention inhibit the proliferation of certain malignant cells. This method is described in J. Natl. Cancer Inst. 60 (1978) 1035–1041, Experimental Cell Research 117 (1978) 15–22 and Proc. Natl. Acad. Sci. USA 77 (1980) 2937–2940.

The antiarthritic effect of the compounds according to the invention can be determined in a conventional manner in animal experiments using the adjuvant arthritis or Streptococci cell wall induced arthritis model. The dermatological activity, for example for the treatment of acne, can be demonstrated, inter alia, by the comedolytic activity and the ability to reduce the number of cysts in the rhino mouse model.

The latter method is described by L. H. Kligman et al. in the Journal of Investigative Dermatology 73 (1978) 354–358. The dermatological activity can also be measured by the reduction in sebaceous glands and the associated diminution in sebum production by the flank organ of the hamster. This method is described by E. C. Gomez in J. Am. Dermatol. 6 (1982) 746–750.

Furthermore, it is possible to determine the reversal which can be achieved with compounds according to the invention of skin damage caused by UV light in animal models. This method is described by L. H. Kligman et al. in Connect. Tissue Res. 12 (1984) 139–150 and in the Journal of the American Academy of Dermatology 15 (1986) 779–785.

Accordingly, the invention furthermore relates to therapeutic agents for topical and systemic administration and to cosmetic agents which contain a compound of the formula I as active substance in addition to conventional carriers or diluents.

The agents can accordingly be administered orally, parenterally or topically. Examples of suitable formulations are uncoated or (film-)coated tablets, capsules, pills, powders, solutions or suspensions, infusion or injection solutions and pastes, ointments, gels, creams, lotions, dusting powders, solutions or emulsions and sprays.

The therapeutic or cosmetic agents can contain the compounds to be used according to the invention in a concentration of 0.001 to 1%, preferably 0.001 to 0.1%, for local use, and preferably in a single dose of 0.1 to 250 mg for systemic use as a therapeutic agent, and are administered in one or more doses each day depending on the nature and severity of the disorders.

The drugs and cosmetics of the invention are produced in a conventional manner with a suitable dosage in accordance with the desired mode of administration using the conventional solid or liquid carriers or diluents and the auxiliaries conventionally used in pharmaceutical technology.

Tablets can be obtained, for example, by mixing the active substance with known auxiliaries, for example inert diluents such as dextrose, sugar, sorbitol, mannitol or polyvinylpyrrolidone, disintegrants such as corn starch or alginic acid, binders such as starch or gelatin, lubricants such as magnesium stearate or talc and/or agents to achieve a depot effect, such as carboxypolymethylene, carboxymethylcellulose, cellulose acetate phthalate or polyvinyl acetate. The tablets can also be composed of several layers.

Similarly, coated tablets can be produced by coating cores, which have been produced in a similar manner to the tablets, with conventional coating agents, for example polyvinylpyrrolidone or shellac, gum arabic, talc, titanium dioxide or sugar. The coating can also be composed of several layers, it being possible to use the auxiliaries mentioned above for tablets.

Solutions or suspensions containing the active substance according to the invention can additionally contain taste corrigents such as saccharin, cyclamate or sugar as well as, for example, flavorings such as vanillin or orange extract. They can moreover contain suspending auxiliaries such as sodium carboxymethylcellulose or preservatives such as p-hydroxybenzoates. Capsules containing active substances can be produced, for example, by the active substance being mixed with an inert carrier such as lactose or sorbitol and encapsulated in gelatin capsules.

Examples of conventional ingredients of cosmetic and pharmaceutical formulations for topical use are: anionic, cationic and nonionic emulsifiers and emulsion stabilizers which can simultaneously act as bodying agents or gel formers, such as polyvinylpyrrolidone, fatty alcohols, glycerol monostearate, polyacrylic acids, cellulose derivatives and ethylene oxide/propylene oxide block polymers, solid or liquid oily components or fats of mineral, vegetable or animal origin, synthetic oily esters such as triglyceride esters and isopropyl myristate, and hydrophilic components such as glycerol, polyethylene glycol and propylene glycol.

Examples of further ingredients of cosmetics are sunscreen agents, suntan agents, preservatives, antioxidants, pigments, colorants, essential oils and perfume oils, vitamins, plant extracts, collagen etc. These substances are described, for example, in the CTFA Cosmetic Ingredient Dictionary, 3rd edition, Washington 1982.

PREPARATION OF THE STARTING COMPOUNDS

Example A 5,6,7,8-tetrahydro-5,5,8,8-tetramethyl-2-naphthyloxirane 66 g (0.3 mol) of trimethylsulfoxonium iodide were added to 34 g (0.3 mol) of potassium tert-butanolate in 300 ml of dry dimethyl sulfoxide at 20°–25° C. and, after 30 min, a solution of 65 g (0.3 mol) of 2-formyl-5,6,7,8-tetrahydro-5,5,8,8-tetramethylnaphthalene in 100 ml of dry dimethyl sulfoxide and 200 ml of dry tetrahydrofuran was added dropwise. After the reaction was complete, the mixture was poured into ice-water and extracted with ether, the organic phase was washed with water and dried over magnesium sulfate, and the solvent was removed under reduced pressure. The residue yielded 60 g of the title compound as a yellowish oil.

$^1$H NMR (CDCl$_3$): $\delta = 3.8$ (t,1H)

Example B

Methyl phenyloxirane-4-carboxylate

In a similar manner to Example A, 37 g of the title compound were prepared as a yellowish oil from 49.0 g (0.3 mol) of methyl 4-formylbenzoate.

$^1$H NMR (CDCl$_3$): $\delta = 3.2$ (dd,1H)

Example C

Methyl ω-bromoacetophenone-4-carboxylate

To 13.5 g (82 mmol) of acetophenone-4-carboxylic acid in 100 ml of dimethylformamide were added 13.8 g (100 mmol) of anhydrous potassium carbonate and, after 30 min, dropwise 12.6 g (100 mmol) of dimethyl sulfate. After the reaction solution had been stirred at 60° C. for 1 h and cooled it was poured into water, and the precipitate was filtered off with suction, washed with water and dried. 11.6 g of methyl acetophenone-4-carboxylate were obtained. 0.6 ml (10 mmol) of bromine was added dropwise to 1.8 g (10 mmol) of this ester in 20 ml of glacial acetic acid at room temperature. After the reaction was complete, the mixture was poured into water, and the precipitate was filtered off and washed with water and yielded, after drying, 2.3 g of the title compound. The carborylic acid obtained from it by alkaline saponification melted at 190°–192° C.

Example D

ω-chloro-5,6,7,8-tetrahydro-5,5,8,8-tetramethyl-2-acetonaphthone 34 g (0.18 mol) of 1,2,3,4-tetrahydro-1,1,4,4-tetramethylnaphthalene dissolved in 100 ml of dry methylene chloride were added dropwise, at 0°–5° C., to a suspension of 36 g (0.27 mol) of anhydrous aluminum chloride in 135 ml of dry methylene chloride and 14 ml (0.18 mol) of chloroacetyl chloride. The mixture was stirred at room temperature overnight and subsequently poured into ice-water. The organic phase was separated off, washed with water and saturated brine, dried over magnesium sulfate and evaporated under reduced pressure. The residue yielded 43 g of the title compound as a yellowish oil.

$^1$H NMR (CDCl$_3$): $\delta = 1.3$ (12H), 1.66 (4H), 4.7 (2H)

Example E 2,2,5,7,8-pentamethylchroman-6-ol 257 g (1.69 mol) of 2,3,6-trimethylhydroquinone were introduced into a suspension of 248 g (1.86 mol) of anhydrous aluminum chloride in 850 ml of dry dichloromethane at 5° C. After stirring for 30 min, 160 g (1.86 mol) of 3-methyl-2-buten-1-ol were added dropwise at 5°–10° C. The mixture was stirred at room temperature overnight and then poured into ice-water, the precipitate was filtered off, the filtrate was extracted with dichloromethane, and the organic phase was washed with water to neutrality, dried over magnesium sulfate and evaporated. Distillation of the residue provided a main fraction of 153.3 g of the title compound at 140° C. and 0.4 mbar, and this was recrystallized from heptane with a melting point of 85°–88° C.

A further 10.3 g of the product were isolated from the original precipitate.

Example F 3,5-di-tert-butylthiophenol

A solution of 103.2 g (0.5 mol) of 3,5-di-tert-butylphenol in 150 ml of dimethylformamide was added dropwise to a stirred suspension of 26.5 g (0.6 mol) of sodium hydride (approx. 60% suspension in mineral oil from which the oil had been removed with pentane) in 200 ml of dry dimethylformamide at room temperature. After evolution of hydrogen had ceased, 67.5 g (0.55 mol) of N,N-dimethylthiocarbamoyl chloride in 100 ml of dimethylformamide were added dropwise, and the reaction solution was stirred at 70° C. for 1 hour and then stirred into 500 ml of cold 5% strength potassium hydroxide solution, and the precipitate was filtered off, washed and dried. 84 g of this product were heated at 320° C. under nitrogen for 30 min. The solidified melt was recrystallized from diisopropyl ether to provide 42 g of a colorless solid (melting point 103°–105° C.) which was dissolved in 200 ml of ether and added dropwise at room temperature to a suspension of 7 g (0.18 mol) of lithium aluminum hydride in 800 ml of ether. After the reaction was complete, 100 ml of 2N hydrochloric acid were added to the mixture, and the ether phase was separated off, washed with water, dried over magnesium sulfate and evaporated under reduced pressure. The residue provided 28.8 g of the title compound of melting point 47°–49° C.

Example G 5,6,7,8-Tetrahydro-5,5,8,8-tetramethyl-2-naphthol 27.5 g (0.2 mol) of anhydrous aluminum chloride were added by spatula to 250.0 g (2.65 mol) of phenol plus 414.5 g (2.27 mol) of 2,5-dichloro-2,5-dimethylhexane in 500 ml of petroleum ether at room temperature while stirring. After 48 hours, the reaction mixture was poured into ice-water and extracted with ether, and the organic phase was washed to neutrality with water, dried over sodium sulfate and evaporated under reduced pressure. Two recrystallizations of the residue from methanol yielded 148.7 g of the title compound of melting point 219°–220° C.

Example H 5,6,7,8-Tetrahydro-5,5,8,8-tetramethyl-2-naphthylamine 77.2 ml of glacial acetic acid and 20.8 ml of nitric acid (98% strength) were mixed while cooling and then added dropwise within 2 hours to a solution of 65.8 g (0.35 mol) of 1,2,3,4-tetrahydro-1,1,4,4-tetramethylnaphthalene in 154 ml of glacial acetic acid and 257 ml of acetic anhydride in a salt/ice bath. After the addition was complete, the reaction mixture was warmed to room temperature and stirred overnight. The solution was then poured into water, and the precipitate was filtered off with suction, washed with water and dried. 79.7 g of crude 2-nitro-5,6,7,8-tetrahydro-5,5,8,8-tetramethylnaphthalene of melting point 46–°50° C. were obtained.

25 g of this crude product were hydrogenated in a mixture of 65 ml of dioxane, 65 ml of methanol and 5 ml of water on 0.3 g of palladium on active carbon (10%) at 100° C. and under 200 bar of hydrogen in an autoclave for 48 hours. After the reaction was complete, the catalyst was filtered off, and the solution was evaporated. Recrystallization of the residue from n-heptane yielded 17.6 g of the title compound of melting point 63°–65° C.

EXAMPLE J 5,6,7,8-Tetrahydro-5,5,8,8-tetramethyl-2-thionaphthol 94.0 g (0.5 mol) of 1,2,3,4-tetrahydro-1,1,4,4-tetramethylnaphthalene were stirred into 100 ml of chlorosulfonic acid at 20° C. within 30 min. The reaction solution was maintained at 60° C. for 1 hour, cooled to room temperature and then poured into 1.5 l of ice and extracted with ether. The organic phase was washed to neutrality with brine and water, dried over magnesium sulfate and evaporated under reduced pressure. Recrystallization of the residue from methanol yielded 55.0 g of 5,6,7,8-tetrahydro-5,5,8,8-tetramethylnaphthalene-2-sulfonyl chloride of melting point 71°–74° C.

57.5 g (0.2 mol) of this sulfonyl chloride in 150 ml of dry tetrahydrofuran were added dropwise at room temperature within 2 hours to a suspension of 15.4 g (0.4 mol) of lithium aluminum hydride in 150 ml of dry tetrahydrofuran. The reaction solution was stirred at room temperature for 1 hour, and then 25 ml of water followed by 50 ml of saturated tartaric acid solution were added dropwise, and the mixture was boiled for a few minutes. The solution was cooled, anhydrous magnesium sulfate was added until clear, and the precipitate was filtered off with suction.

Evaporation of the filtrate yielded 33.0 g of the title compound as a resin ($R_f$=0.4, 7:3 heptane/ethyl acetate).

Preparation of the Compounds According to the Invention

Example 1

1-(4-methoxycarbonylphenyl)-2-(5,6,7,8-tetrahydro-5,5,8,8-tetramethyl-2-naphthylthio)ethanol 2.2 g (10 mmol) of 5,6,7,8-tetrahydro-5,5,8,8-tetramethyl-2-thionaphthol (from Example J) and 1.78 g (10 mmol) of methyl phenyloxirane-4-carboxylate (from Example B) were stirred with 15 g of basic alumina (Woelm) in 50 ml of toluene at room temperature. After the reaction was complete, the solution was filtered and evaporated under reduced pressure. The residue was chromatographed on 30 g of silica gel (heptane/ethyl acetate=95:5) to provide 0.4 g of the title compound as a colorless oil.

$^1$H NMR (CDCl$_3$): δ=3.22 (d,2H); 3.84 (s,3H); 4.79 (m,1H)

Example 2

1-(4-methoxycarbonylphenyl)-2-(5,6,7,8-tetrahydro-5,5,8,8-tetramethyl-2-naphthyloxy)ethanol 2 g (10 mmol) of 5,6,7,8-tetrahydro-5,5,8,8-tetramethyl-2-naphthol (from Example G) and 1.78 g (10 mmol) of methyl phenyloxirane-4-carboxylate (from Example B) were refluxed with 7 g (50 mmol) of potassium carbonate and 10 g of alumina in 50 ml of toluene. After the reaction was complete, the solution was filtered, the filtrate was evaporated, and the residue was chromatographed on 14 g of silica gel (haptane/ethyl acetate 95:5).

0.3 g of the title compound of melting point 92°–96° C. was obtained.

Example 3

1-(5,6,7,8-tetrahydro-5,5,8,8-tetramethyl-2-naphthyl)-2-(4-carboxyphenylthio)ethanone 26.5 g (0.1 mol) of ω-chloro-5,6,7,8-tetrahydro-5,5,8,8-tetramethyl-2-acetonaphthone (from Example D) in 100 ml of dimethylformamide were added dropwise to a solution of 15.0 g (0.1 mol) of 4-mercaptobenzoic acid and 22.0 g (0.22 mol) of triethylamine in 200 ml of dimethylformamide at 0°–5° C. After the reaction solution had been stirred for 2 h it was poured into water, the pH was adjusted to 4 with dilute hydrochloric acid, and the precipitate was filtered off with suction, washed with water and methanol and dried. Recrystallization from methanol provided 16.2 g of the title compound of melting point 175°–179° C. A further 2.2 g of pure product were obtained from the mother liquor.

Example 4

1-(5,6,7,8-tetrahydro-5,5,8,8-tetramethyl-2-naphthyl)-2-(4-carboxyphenylthio)ethanone S,S-dioxide 5 ml (30 mmol) of hydrogen peroxide (30% strength aqueous solution) were added dropwise to 5.0 g (13 mmol) of 1-(5,6,7,8-tetrahydro-5,5,8,8-tetramethyl-2-naphthyl)-2-(4-carboxyphenylthio)ethanone (from Example 3) in 100 ml of glacial acetic acid at 50° C., and the mixture was maintained at 75° C. for 1 h. The reaction solution was cooled and poured into dilute brine, and the precipitate was filtered off with suction, dried and chromatographed on 35 g of silica gel (methylene chloride/methanol=98:2), providing 2.0 g of the title compound, which crystallized from heptane/ethyl acetate with melting point 156°–160° C.

Example 5

1-(5,6,7,8-tetrahydro-5,5,8,8-tetramethyl-2-naphthyl)-2-(4-ethoxycarbonylphenoxy)ethanone 6.6 g (55 mmol) of potassium tert-butanolate were added by spatula to 14.3 g (55 mmol) of ω-chloro-5,6,7,8-tetrahydro-5,5,8,8-tetramethyl-2-acetonaphthone (from Example D) in 220 ml of dimethylformamide. At room temperature a solution of 9.1 g (55 mmol) of ethyl 4-hydroxybenzoate in 33 ml of dimethylformamide was added dropwise and, after the reaction was complete, the mixture was poured into water and extracted with ether; the extracts were washed with water, dried over magnesium sulfate and evaporated. The oily residue was purified by chromatography (heptane/ethyl acetate 85:15) and crystallization from methanol to provide 16.4 g of the title compound of melting point 105°–107° C.

Example 6

1-(5,6,7,8-tetrahydro-5,5,8,8-tetramethyl-2-naphthyl)-2-(4-carboxyphenoxy)ethanone 6 g (15 mmol) of 1-(5,6,7,8-tetrahydro-5,5,8,8-tetramethyl-2-naphthyl)-2-(4-ethoxycarbonylphenoxy)ethanone (from Example 5) were stirred with 5 g of potassium hydroxide in 90 ml of ethanol/water/dimethyl sulfoxide (5:3:1) at 80° C. for 5 min and poured into ice-water, the alkaline solution was extracted with ether and the extract was discarded, and then the pH was adjusted to 3 with concentrated hydrochloric acid, and the acid solution was extracted with ethyl acetate. The latter extract was washed with water, dried over magnesium sulfate and evaporated. Recrystallization of the residue from ethanol provided 2.8 g of the title compound of melting point 168°–170° C.

Example 7

1-(5,6,7,8-tetrahydro-5,5,8,8-tetramethyl-2-naphthyl)-2-(4-carboxyphenoxy)ethanol 2.1 g (5 mmol) of 1-(5,6,7,8-tetrahydro-5,5,8,8-tetramethyl-2-naphthyl)-2-(4-ethoxycarbonylphenoxy)ethanone (from Example 5) in 100 ml of tetrahydrofuran/methanol (2:1) were stirred with 0.4 g (10 mmol) of sodium borohydride at room temperature for 30 min; the reaction solution was poured into saturated brine and extracted with ethyl acetate; the extracts were washed with water, dried over magnesium sulfate and evaporated to provide an oily residue which was subjected to alkaline hydrolysis as described in Example 6 and yielded after appropriate working up 1.4 g of the title compound; melting point (cyclohexane): 160°–162° C.

Example 8

1-(5,6,7,8-tetrahydro-5,5,8,8-tetramethyl-2-naphthyl)-2-(4-carboxyphenylamino)ethanone 25.5 ml (0.5 mol) of bromine were added dropwise to 115 g (0.5 mol) of 5,6,7,8-tetrahydro-5,5,8,8-tetramethyl-2-acetonaphthone in 100 ml of glacial acetic acid, to which 4 drops of hydrobromic acid in glacial acetic acid (30% strength solution) had been added, at 30° C. and, after the reaction was complete, the mixture was introduced into 1.5 l of ice-water. Extraction with methylene chloride, washing of the extracts with water and dilute sodium bicarbonate solution, drying over sodium sulfate and evaporation of the solvent provided 90 g of an oily crude product. 48 g of this were taken up in 80 ml of dimethylformamide and added dropwise to a suspension of 25 g (0.18 mol) 4-aminobenzoic acid and 40 g (0.4 mol) of triethylamine in 70 ml of dimethylformamide while cooling in an ice bath. After the mixture had been stirred at room temperature for 3 h, 200 ml of water were added dropwise. The brown precipitate was evaporated off and recrystallized from methanol/tetrahydrofuran to provide 16.7 g of the title compound of melting point 168°–169° C.

Example 9

1-(4-methoxycarbonylphenyl)-2-(5,6,7,8-tetrahydro-5,5,8,8-tetramethyl-2-naphthylthio)ethanone To 2.0 g (9 mmol) of 5,6,7,8-tetrahydro-5,5,8,8-tetramethyl-2-thionaphthol in 30 ml of dimethylformamide were added 1.2 g (10 mmol) of potassium tert-butanolate by spatula and subsequently, at room temperature, dropwise 2.3 g (9 mmol) of ω-bromo-4-methoxycarbonylacetophenone (from Example C). After 30 min, the reaction solution was introduced into water and extracted with ether; the extracts were washed with water and dried over magnesium sulfate, and evaporation of the solvent provided a residue which was digested with heptane to produce 1.3 g of the title compound as an oil.

$^1$H NMR (CDCl$_3$: δ = 3.95 (s,3H); 4.2 (s,2H)

TABLE

| Beispiel Nr. | R$^1$ | R$^2$ | R$^3$ | R$^4$ | R$^5$ | A | R$^6$ | Schmp. (°C.) |
|---|---|---|---|---|---|---|---|---|
| 10 | H | H | H | —C(CH$_3$)$_2$CH$_2$CH$_2$C(CH$_3$)$_2$— | | —CHOH—CH$_2$—S— | —CO$_2$H | 158–160 |
| 11 | H | H | H | —C(CH$_3$)$_2$CH$_2$CH$_2$C(CH$_3$)$_2$— | | —CHOH—CH$_2$—NH— | —CO$_2$H | 96–104 |
| 12 | H | H | H | —C(CH$_3$)$_2$CH$_2$CH$_2$C(CH$_3$)$_2$— | | —S—CH$_2$—CHOH— | —OC(CH$_3$)$_3$ | |
| 13 | H | H | C(CH$_3$)$_3$ | H | C(CH$_3$)$_3$ | —O—CH$_2$—CHOH— | —OC(CH$_3$)$_3$ | |
| 14 | H | H | C(CH$_3$)$_3$ | H | C(CH$_3$)$_3$ | —O—CH$_2$—CHOH— | —OH | |
| 15 | H | H | C(CH$_3$)$_3$ | H | C(CH$_3$)$_3$ | —O—CH$_2$—CHOH— | —OC(O)CH$_3$ | |
| 16 | H | H | H | —C(CH$_3$)$_2$CH(CH$_3$)C(CH$_3$)$_2$— | | —NH—CH$_2$—CHOH— | —OC(CH$_3$)$_3$ | 139–142 |
| 17 | H | H | H | —C(CH$_3$)$_2$CH$_2$CH$_2$C(CH$_3$)$_2$— | | —O—CH$_2$—CHOH— | —SCH$_3$ | |
| 18 | H | H | C(CH$_3$)$_3$ | H | C(CH$_3$)$_3$ | —O—CH$_2$—CHOH— | —SCH$_3$ | 70–73 |
| 19 | CH$_3$ | CH$_3$ | CH$_3$ | —OC(CH$_3$)$_2$CH$_2$CH$_2$— | | —O—CH$_2$—CHOH— | —SCH$_3$ | |
| 20 | H | H | C(CH$_3$)$_3$ | H | C(CH$_3$)$_3$ | —O—CH$_2$—CHOH— | —S(O)$_2$C$_2$H$_5$ | |
| 21 | H | H | C(CH$_3$)$_3$ | H | C(CH$_3$)$_3$ | —O—CH$_2$—CHOH— | —CN | 119–122 |
| 22 | H | H | C(CH$_3$)$_3$ | H | C(CH$_3$)$_3$ | —O—CH$_2$—CHOH— | —CH$_2$NH$_2$ | 148–150 |
| 23 | H | H | H | —C(CH$_3$)$_2$CH$_2$CH$_2$C(CH$_3$)$_2$ | | —S—CH$_2$—CHOH— | —NHC(O)CH$_3$ | |
| 24 | CH$_3$ | CH$_3$ | CH$_3$ | —OC(CH$_3$)$_2$CH$_2$CH$_2$— | | —O—CH$_2$—COOH— | —NHC(O)CH$_3$ | |
| 25 | H | H | C(CH$_3$)$_3$ | H | C(CH$_3$)$_3$ | —O—CH$_2$—C(O)— | —NO$_2$ | 117–119 |
| 26 | H | H | H | —C(CH$_3$)$_2$C$_2$H$_5$ | H | —O—CH$_2$—C(O)— | —NO$_2$ | |
| 27 | H | C(CH$_3$)$_3$ | H | —C(CH$_3$)$_3$ | CH$_3$ | —O—CH$_2$—C(O)— | —NO$_2$ | |
| 28 | H | CH(CH$_3$)C$_2$H$_5$ | H | —C(CH$_3$)$_3$ | H | —O—CH$_2$—C(O)— | —NO$_2$ | |
| 29 | H | CH$_3$ | H | —C(CH$_3$)$_3$ | H | —S—CH$_2$—C(O)— | —NO$_2$ | 90–91 |
| 30 | H | H | C(CH$_3$)$_3$ | —OH | C(CH$_3$)$_3$ | —O—CH$_2$—C(O)— | —NO$_2$ | |
| 31 | H | H | C(CH$_3$)$_3$ | H | C(CH$_3$)$_3$ | —S—CH$_2$—CHOH— | —OCOCH$_3$ | |
| 32 | H | H | C(CH$_3$)$_3$ | H | C(CH$_3$)$_3$ | —O—CH$_2$—CHOH— | —H | |
| 33 | CH$_3$ | CH$_3$ | CH$_3$ | —OC(CH$_3$)$_2$CH$_2$CH$_2$— | | —O—CH$_2$—CHOH— | —H | |
| 34 | H | H | C(CH$_3$)$_3$ | H | C(CH$_3$)$_3$ | —O—CH$_2$—COOH— | 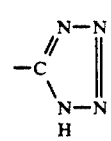 | |
| 35 | H | H | C(CH$_3$)$_3$ | H | C(CH$_3$) | —O—CH$_2$—CHOH— | —CHO | |
| 36 | H | H | C(CH$_3$)$_3$ | H | C(CH$_3$)$_3$ | —O—CH$_2$—CHOH— | —CH$_2$OH | |
| 37 | H | H | C(CH$_3$)$_3$ | H | C(CH$_3$)$_3$ | —O—CH$_2$—CHOH— | 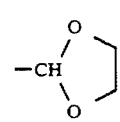 | |

TABLE-continued

| Beispiel Nr. | R¹ | R² | R³ | R⁴ | R⁵ | A | R⁶ | Schmp. (°C.) |
|---|---|---|---|---|---|---|---|---|
| 38 | H | H | C(CH₃)₃ | H | C(CH₃)₃ | —O—CH₂—CHOH— | —SO₃H | |
| 39 | H | H | C(CH₃)₃ | H | C(CH₃)₃ | —O—CH₂—CHOH— | —SH | |
| 40 | H | H | C(CH₃)₃ | H | C(CH₃)₃ | —O—CH₂—CHOH— | —COCH₃ | |
| 41 | H | H | C(CH₃)₃ | H | C(CH₃)₃ | —O—CH₂—C(O)— | —C(O)NHOH | |

EXAMPLES OF PHARMACEUTICAL FORMULATIONS

Example I

Tablet Containing 250 mg of Active Substance

Composition for 1000 tablets:
Active substance of Example No. 2: 250 g
Potato starch: 100 g
Lactose: 50 g
4% gelatin solution: 45 g
Talc: 10 g Preparation:

The finely powdered active substance, potato starch and lactose are mixed. The mixture is moistened with about 45 g of 4% strength aqueous gelatin solution, converted into fine granules and dried. The dry granules are screened, mixed with 10 g of talc and compressed to tablets in a rotary tableting machine. The tablets are packed into tightly sealable polypropylene containers.

Example II

Cream Containing 0.1% Active Substance

Active substance of Example No. 10: 0.1 g
Glycerol monostearate: 10.0 g
Cetyl alcohol: 4.0 g
Polyethylene glycol 400 stearate: 10.0 g
Polyethylene glycol sorbitan monostearate: 10.0 g
Propylene glycol: 6.0 g
Methyl p-hydroxybenzoate: 0.2 g
Demineralized water: ad 100.0 g Preparation:

The very finely powdered active substance is suspended in propylene glycol and the suspension is stirred into the molten mixture of glycerol monostearate, cetyl alcohol, polyethylene glycol 400 stearate and polyethylene glycol sorbitan monostearate at 65° C. A solution of methyl p-hydroxybenzoate in water at 70° C. is emulsified in this mixture. After the cream has cooled it is homogenized in a colloid mill and packed into tubes.

Example III

Dusting Powder Containing 0.1% Active Substance

Active substance of Example No. 11: 0.1 g
Zinc oxide: 10.0 g
Magnesium oxide: 10.0 g
Highly disperse silica: 2.5 g
Magnesium stearate: 1.0 g
Talc: 76.4 g Preparation:

The active substance is micronized and mixed homogeneously with the other ingredients in an air-jet mill. The mixture is forced through a screen (mesh No. 7) and packed into polyethylene containers with a sprinkle top.

We claim:

1. An oxidized diphenylheteroalkane of the formula I

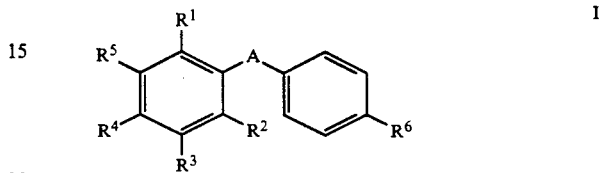

where A is one of the following: —CHOH—CH₂X— or —C(O)— CH₂X—, where X can be bonded to the right or left of the two phenyl rings and is oxygen, —S(O)$_n$— (with n being 0, 1 or 2) or NH, R¹, R² and R³ are, independently of one another, hydrogen or C₁-C₄-alkyl, R⁴ and R⁵ are, independently of one another, hydrogen, C₁-C₅-alkyl or together, with the formation of a ring, —C(CH₃)₂—B—C(CH₃)₂— (with B being —CH₂CH₂— or —CH(CH₃)—) or —OC(CH₃)(Z)CH₂CH₂— (with Z being C₁-C₂-alkyl which can be substituted by —OR⁹), and R⁴ is additionally —OR⁹, where R⁴ and R⁵ together form a ring of the said type when R¹ to R³ are hydrogen, and R⁴ and R⁵ together form a ring of the said type, or R³ and R⁵ are each branched C₃- or C₄-alkyl when R⁶=H, OH, SH or CH₃, R⁶ is hydrogen, methyl, cyano, tetrazolyl or —CH₂OR⁹, —OR¹⁰, —NR¹¹R¹², —CH₂NR¹¹R¹², —CH(R¹³)₂, —S(O)$_m$R¹⁴ (with m=1 or 2), —SR¹⁰, —SO₃H or —COR¹⁵, where R⁹ is hydrogen, C₁₋₆-alkyl or C₁₋₆-alkanoyl, R¹⁰ is hydrogen, C₁₋₆-alkyl, C₁₋₆-alkanoyl or benzoyl or —CH₂COR⁷ (with R⁷ being hydrogen, C₁₋₆-alkyl, C₁₋₆-alkoxy or hydroxyl), R¹¹ and R¹² are, independently of one another, hydrogen, C₁₋₄-alkyl, C₁₋₄-alkanoyl or benzyl or benzoyl, R¹³ is C₁₋₆-alkoxy, it being possible for two R¹³ radicals to form together with the CH a cyclic 5- or 6-membered acetal, R¹⁴ is C₁₋₆-alkyl, R¹⁵ is hydrogen, hydroxyl, C₁₋₆-alkyl, C₁₋₆-alkoxy, phenoxy or benzyloxy, —NR¹¹R¹² with R¹¹ and R¹² being hydrogen, alkyl, or benzyl which can be substituted by hydroxyl or C₁₋₄-alkoxy, or —NR¹⁶OR¹⁷ (with R¹⁶ and R¹⁷=hydrogen or C₁-C₃-alkyl), and the physiologically tolerated salts thereof.

2. An oxidized diphenylheteroalkane of the formula I as claimed in claim 1, where X is oxygen, sulfur or NH, and R⁴ and R⁵ together are a ring of the type mentioned in claim 1, or R³ and R⁵ are each a branched C₃- or C₄-alkyl.

3. An oxidized diphenylheteroalkane of the formula I as claimed in claim 1, where R⁶ is —CH₂OR⁹, —OR¹⁰, —SR¹⁰, —SO₂R¹⁴, —SO₃H or —COR¹⁵.

4. An oxidized diphenylheteroalkane of the formula I as claimed in claim 1, where X, R⁴ and R⁵ are as defined in claim 2, and R⁶ is —CH₂OR⁹, —OR¹⁰, —SR¹⁰, —SO₂R¹⁴, —SO₃H or —COR¹⁵.

* * * * *